(12) United States Patent
Stahl et al.

(10) Patent No.: US 9,216,829 B2
(45) Date of Patent: Dec. 22, 2015

(54) SYSTEM AND METHOD FOR RIGGING A CONTROL SURFACE OF AN AIRCRAFT

(71) Applicant: Airbus Operations GmbH, Hamburg (DE)

(72) Inventors: Gerd Stahl, Hamburg (DE); Frank Dierenfeldt, Hamburg (DE); Denis Oegretici, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 287 days.

(21) Appl. No.: 13/921,555

(22) Filed: Jun. 19, 2013

(65) Prior Publication Data

US 2014/0007397 A1 Jan. 9, 2014

Related U.S. Application Data

(60) Provisional application No. 61/668,493, filed on Jul. 6, 2012.

(30) Foreign Application Priority Data

Jul. 6, 2012 (EP) .................................... 12175391

(51) Int. Cl.
  *B64C 1/26* (2006.01)
  *G01B 11/00* (2006.01)
  (Continued)

(52) U.S. Cl.
  CPC ................. *B64F 5/0009* (2013.01); *B64C 1/26* (2013.01); *G01B 11/00* (2013.01);
  (Continued)

(58) Field of Classification Search
  CPC . G01B 11/00; G01B 21/00; G01B 2021/0162

USPC ...................... 356/237.1–241.6, 242.1–243.8, 356/426–431, 600–640
See application file for complete search history.

(56) References Cited

U.S. PATENT DOCUMENTS

| | | | | |
|---|---|---|---|---|
| 3,478,569 A | * | 11/1969 | Aichinger | B64F 5/0009 340/974 |
| 4,489,591 A | * | 12/1984 | Myrick | G01P 21/00 73/1.78 |
| 6,801,257 B2 | * | 10/2004 | Segev | G01C 11/06 348/296 |

(Continued)

FOREIGN PATENT DOCUMENTS

DE 7208763 C 5/1942

OTHER PUBLICATIONS

European Searching Authority, European Search Report for 12175391.7 Mailed Dec. 10, 2012.

*Primary Examiner* — Gregory J Toatley
*Assistant Examiner* — Jarreas C Underwood
(74) *Attorney, Agent, or Firm* — Ingrassia Fisher & Lorenz, P.C.

(57) ABSTRACT

A system for rigging a control surface of an aircraft, wherein the control surface is movable relative to a reference structure of the aircraft by means of at least one actuator, comprises a mobile control unit having being connectable to at least one actuator, an input means for commanding a deflection of the control surface, and an optical rigging apparatus having a first rigging component and a second rigging component. The first rigging component is adapted for being mounted on a reference structure to which the control surface is swivably attached and the second rigging component is adapted for being mounted on the control surface itself. Thereby an accurate rigging may be conducted with a clearly reduced number of personnel and a clearly reduced time for completion.

19 Claims, 3 Drawing Sheets

(51) Int. Cl.
  *G01N 21/00* (2006.01)
  *B64F 5/00* (2006.01)
  *G01N 21/01* (2006.01)
  *G01B 11/06* (2006.01)

(52) U.S. Cl.
  CPC ........... *G01B 11/0691* (2013.01); *G01N 21/00* (2013.01); *G01N 2021/0162* (2013.01); *Y10T 29/49769* (2015.01); *Y10T 29/5313* (2015.01)

(56) References Cited

U.S. PATENT DOCUMENTS

| | | | |
|---|---|---|---|
| 7,338,018 B2* | 3/2008 | Huynh | B64C 9/16 244/215 |
| 7,978,322 B2* | 7/2011 | Marsh | G01B 11/272 250/231.13 |
| 2010/0085437 A1* | 4/2010 | Troy | G01S 5/163 348/211.7 |

* cited by examiner

SYSTEM AND METHOD FOR RIGGING A CONTROL SURFACE OF AN AIRCRAFT

CROSS-REFERENCE TO RELATED APPLICATIONS

This application claims priority to European Patent Application No. EP 12 175 391.7, filed Jul. 6, 2012, and to U.S. Provisional Patent Application No. 61/668,493, filed Jul. 6, 2012, which are each incorporated herein by reference in their entirety.

TECHNICAL FIELD

The technical field relates to a system and a method for rigging a control surface of an aircraft.

BACKGROUND

Control surfaces that are movably connected to a reference structure and that are adjustable through a linear and/or rotary actuator are commonly used on aircraft for providing a variety of different flight mechanical tasks. For example, it is common to use an elevator that is pivotably connected to the trailing edge of a horizontal tailplane, also known as horizontal stabilizer, for generating a pitching moment depending on the extension of an actuator which is connected between the elevator and the horizontal tailplane. During the manufacture of the aircraft, the kinematical relationship which may constitute a three-joint-link between the reference structure, the control surface, and the actuator needs to be adjusted such that a predetermined central initial position and at least one deflected end position of the control surface can be reached by moving the actuator along a predetermined path. This adjustment process usually includes disconnecting the actuator from the control surface, adjusting respective connection means for changing the active length of the actuator, reconnecting the actuator and operating the actuator, accompanied by measuring the resulting motion of the control surface. If the motion of the control surface differs from a predetermined motion, a further adjustment step is necessary and the actuator has to be disconnected and adjusted again. This process is known as rigging.

For conducting the measuring step, in the rigging process for an elevator usually an elongated, bar-like template or reference bar is placed on an upper surface of a horizontal stabilizer that extends over the trailing edge of the elevator. An indicator is thereby positioned in the vicinity of the trailing edge of the elevator, allowing an unobstructed motion thereof and allowing the comparison of reachable end positions of the trailing edge of the elevator and respective markings on the indicator. If the reachable end positions of the trailing edge of the elevator differ from the respective markings a re-adjustment necessary during which the reference bar has to be removed.

During a rigging process, the cockpit of the aircraft is usually blocked by a first person who moves pilot controls upon radio communication and prevents an inadvertent motion of pilot controls through unauthorised personnel to avoid accidents. A second person places and removes the reference bar onto the horizontal stabilizer. A third person mechanically adjusts the kinematical relationship between the horizontal tail plane, the elevator and the actuator by re-adjusting respective connection means.

In addition, other objects, desirable features and characteristics will become apparent from the subsequent summary and detailed description, and the appended claims, taken in conjunction with the accompanying drawings and this background.

SUMMARY

Accordingly, rigging of control surfaces of an aircraft may be a time-consuming process during which no other work can be conducted in the cockpit and on the part of the aircraft where the control surface to be rigged is situated. For increasing the productivity and reducing the costs for assembling an aircraft, it may be desirable to provide a system and a method for rigging a control surface of an aircraft that allows a clear reduction of manpower and blocked time in the cockpit. At the same time, the accuracy for the rigging result at least needs to be maintained.

The system for rigging a control surface of an aircraft, wherein the control surface is movable relative to a reference structure of the aircraft by means of at least one actuator, comprises a mobile control unit being connectable to the at least one actuator. The system furthermore comprises an input means for providing a command signal for moving the control surface to be rigged. The system also comprises an optical rigging apparatus having a first rigging component and a second rigging component, wherein the first rigging component is adapted for being fixed relative to the reference structure of the aircraft and the second rigging component is adapted for being fixed relative to the control surface, wherein the optical rigging apparatus is adapted for providing an indication of relative spatial positions of the first and second rigging components. The mobile control unit is adapted for generating an actuator signal for inducing a motion of the control surface depending on the command signal of the input means.

An aspect of the present disclosure lies in providing the mobile control unit for controlling the deflection of the control surface in the direct surrounding of the control surface that is to be rigged. By means of an actuator interface or any other suitable means the mobile control unit is adapted for having a signal communication to an actuator, either with a wired connection or a wireless connection. Through the use of the input means for moving the control surface an operator is allowed of inducing and measuring or validating changes of the end positions and of a center position of the control surface in its direct vicinity. It thereby is not necessary for a person to block the cockpit of the aircraft just for the purpose of controlling the control surface deflection.

In one example, the connection of any actuator connected to the control surface and a control unit that is installed in or accessible from the cockpit through any control means is temporarily interrupted such that an inadvertent deflection of the respective control surface from command signals generated in the cockpit can be avoided. This may be further supported by switching leak measurement valves. These are commonly installed in an aircraft for closing solenoid valves of a high pressure manifold of a hydraulics system for the purpose of measuring leaks by supplying hydraulic fluid from a ground based supply and measuring leakage volume flows. As blocking the cockpit is not necessary, other testing procedures may be conducted parallel to the rigging process inside the cockpit, hence the completion of ground tests and the final assembly of an aircraft can be clearly accelerated.

Instead of using a large, heavy and awkward reference bar that has to be mounted and dismounted several times onto the reference structure to which the control surface to be rigged is installed, a precise and lightweight optical measurement apparatus is used. Basically, the optical measurement apparatus comprises two rigging components. A first rigging component is adapted for being placed onto a reference structure whereas the second rigging component is adapted for being placed on the control surface, which is swivably attached to the reference structure. The optical measuring is conducted by providing an indication or detection of relative positions between the two rigging components through rays of light. This may be achieved through a plurality of different techniques, such as emitting a laser beam from one of the two components to the other one where it impinges on an indicator surface, an electronic detector or any other means that allow the detection of the position of the impinging rays of light. Alternatively one of the two rigging components may be adapted for emitting rays of light that impinge on a reflecting surface of the other rigging component such that the rays are reflected back onto the light emitting rigging component that may therefore comprise a suitable indicator surface, an electronic indicator or the such. In the latter case, a resolution of the measurement results may be further enhanced.

The use of an optical rigging apparatus is clearly advantageous over using a reference bar as rather long distances between existing or mountable reference points on the reference structures and the control surface do not need to be bridged by a rigid frame but instead through rays of light. The measurement is therefore extremely precise and the two rigging components do not need to be removed and attached between the individual measuring steps as they can be designed with clearly smaller dimensions and a lower weight compared to the reference bar such that they may be maintained on the control surface itself and the reference structure even if the actuator is in the process of being disconnected or re-adjusted. The awkward placement process of the reference bar can therefore be completely eliminated, hence the rigging process is drastically accelerated.

The known reference bars are typically positioned on fixed reference points, e.g. two reference points on the reference structure. The reference points are located at a distance to each other for receiving two mounting points of the reference bar. The remaining part of the reference bar extends over the control surface to be rigged. As the reference bar does not need to be used, at least one of the two reference points on the reference structure may be used for placing one of the two measurement components.

The actuator for a control surface of an aircraft may be a fluid (e.g. hydraulic) actuator or an electric actuator. In both cases a control signal is used for inducing a motion of the actuator, wherein the control signal either induces an action of the actuator directly or opens or closes a valve for enabling an inflow and an outflow of a fluid for moving a piston of a fluid actuator. For being able to transfer the respective control signals to the actuator it is necessary to either connect the valves, a control logic unit or the actuator itself to the mobile control unit, through the use of the actuator interface provided therein. Regarding possible embodiments of the interface more details are given further below.

In one of various embodiments of the present disclosure, the mobile control unit is adapted for generating a valve control signal for controlling at least one actuator valve of the at least one actuator. Thereby, a hydraulic actuator connected to the control surface to be rigged may directly be operated through the mobile control unit. Electronic valve connectors are therefore temporarily disconnected from an original valve control line, bus or network in the aircraft.

In another exemplary embodiment, the mobile control unit is further connectable to a control system of the aircraft. Thereby, the mobile control unit may be hooked up onto a line, a bus or a network of the aircraft in order to transfer command signals as if the pilot controls were moved. For this purpose the control unit installed in the aircraft should be switchable into an operating status that allows overriding original pilot control means.

Alternatively, the actuators are electric actuators and comprise a position command input port that is connected to a line, bus or network connected to a control unit in the aircraft. This connection may temporarily be interrupted and instead the mobile control unit may be connected to this position command input port.

In one of various embodiments of the present disclosure, one of the first and second rigging components comprises a light source adapted for generating rays of light. The other one of the first and second rigging components comprises a light receiver in form of an indication surface, a detector or a reflector. Thereby, an optical measurement may be conducted by directing rays of light from one of the first and second rigging components to the other one where either a light spot becomes visible or is electronically detected or where a reflection of the rays of light to the other rigging component is conducted. In the latter case, an indication surface or an electronic detector may be present on the rigging component that comprises the light source. The position of the light spot on the indication surface may be read out through the use of a scale printed onto the indication surface or automatically through a signal of the electronic detector. During an automatic acquisition of a relative spatial position a signal may be generated representing the position that may be displayed on a screen, which may be integrated into one of the two rigging components and/or on the mobile control unit.

In one embodiment, the optical rigging component may comprise a third rigging component that includes an aperture, wherein the third rigging component is adapted for being fixed relative to the reference structure of the aircraft between the first rigging component and the second rigging component in order to define a straight light beam between the light source and the light receiver. Through an appropriate exact alignment of the first and third rigging component on a reference structure rays of light may only intersect with the aperture and the first rigging component when the control surface is almost exactly in its center position. By providing an appropriate marker or detector on the indication surface the exact neutral position can be indicated. As explained above, two reference points may be present or mountable to the reference structure. The third rigging component may be placed onto the second, unused reference point for being exactly positioned.

In one exemplary embodiment, the mobile control unit comprises a display for indicating a position command of the input means. The mobile control unit may thereby display the same relevant information as instruments or displays inside the cockpit, such that the mobile control unit is an adequate substitution.

In another embodiment, the second rigging component is adapted for being fixed at a trailing edge of the control surface. Due to the largest possible distance of the second rigging component to the swiveling axis a highest possible resolution may be achieved.

Also provided according to various teachings of the present disclosure is a method for rigging a control surface of an aircraft, wherein the control surface is movable relative to a reference structure of the aircraft by means of at least one actuator. The method may comprise the following: Fixing a first rigging component relative to the reference structure to which the respective control surface is attached; fixing a second rigging component relative to the control surface; connecting a mobile control unit to the at least one actuator;

providing a command signal by using input means of the mobile control unit; generating an actuator signal by means of the mobile control unit for inducing a motion of the control surface depending on the provided command signal; indicating a relative spatial position of the first and second rigging components by means of a light beam between the first and second rigging components; and adjusting the relative position between the control surface and the reference structure based on the indicated relative spatial position.

Before conducting the above method the at least one actuator should be disconnected from any control means in the aircraft that is responsible for initiating a motion of the actuator. The disconnection generally includes disconnecting electric control signal ports of the actuator or of fluid control valves that control a fluid inflow and outflow of an actuator. The electric control signal ports will then be connected to the actuator interface of the mobile control unit for the purpose of substituting the control of the actuator or the valves through the mobile control unit. This allows an operator, who wants to adjust the mechanical connection between the actuator and the respective control surface, to move the actuator for a verification of the adjusted mechanical connection directly from where he stands.

Adjusting the relative position between the control surface and the reference structure may be conducted by adjusting a mechanical connection between the actuator and the control surface, e.g. by removing a flange or a fork on the rod of the actuator in question by screwing in or screwing out a respective fastening component. For holding the flange or fork in the desired position, a counternut and a securing wire may be used. Afterwards, the flange or fork may be attached to the control surface again.

Measuring the position of the respective control surface may include emitting rays of light from one of the two rigging components to the other one. By checking the relative position of the ray of light of one of the two measurement devices, generally supported by appropriate indicators or electronic detectors, it may precisely be judged whether the desired position of the respective control surface is reached.

The process of moving the control surface through the mobile control unit, the disconnection and the reconnection as well as the adjustment of the actuator in question are conducted in an iterative manner until the predetermined positions are reached.

If the respective control surface is driven by a plurality of actuators, e.g. two or three hydraulic actuators, connected to different hydraulic systems, the whole process explained above may be repeated for all other actuators. During the movement of one of the plurality of actuators the remaining actuators may be mechanically disconnected from the control surface, disconnected from electric connectors or otherwise prepared to not counteract on the movement of the actuator to be adjusted.

The method may further comprise re-indicating a relative spatial position of the first and second rigging components by means of a light beam between the first and second rigging components after adjusting and re-adjusting the relative position between the control surface and the reference structure based on the re-indicated relative spatial position.

In one embodiment, the method may comprise indicating the command signal on a display of the mobile control unit, wherein the adjusting or re-adjusting is further based on the indicated command signal.

Still further, the method may comprise fixing a third rigging component including an aperture relative to the reference structure of the aircraft between the first rigging component and the second rigging component in order to define the light beam between the light source and the light receiver. The aperture leads to an improved ability for exactly adjusting the control surface relative to the reference structure.

In one embodiment, fixing the second measurement component relative to the control surface includes fixing the second measurement component at a trailing edge of the control surface for increasing the possible measuring accuracy.

A person skilled in the art can gather other characteristics and advantages of the disclosure from the following description of exemplary embodiments that refers to the attached drawings, wherein the described exemplary embodiments should not be interpreted in a restrictive sense.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the present disclosure or the application and uses of the present disclosure. Furthermore, there is no intention to be bound by any theory presented in the preceding background or the following detailed description.

Figure 1:
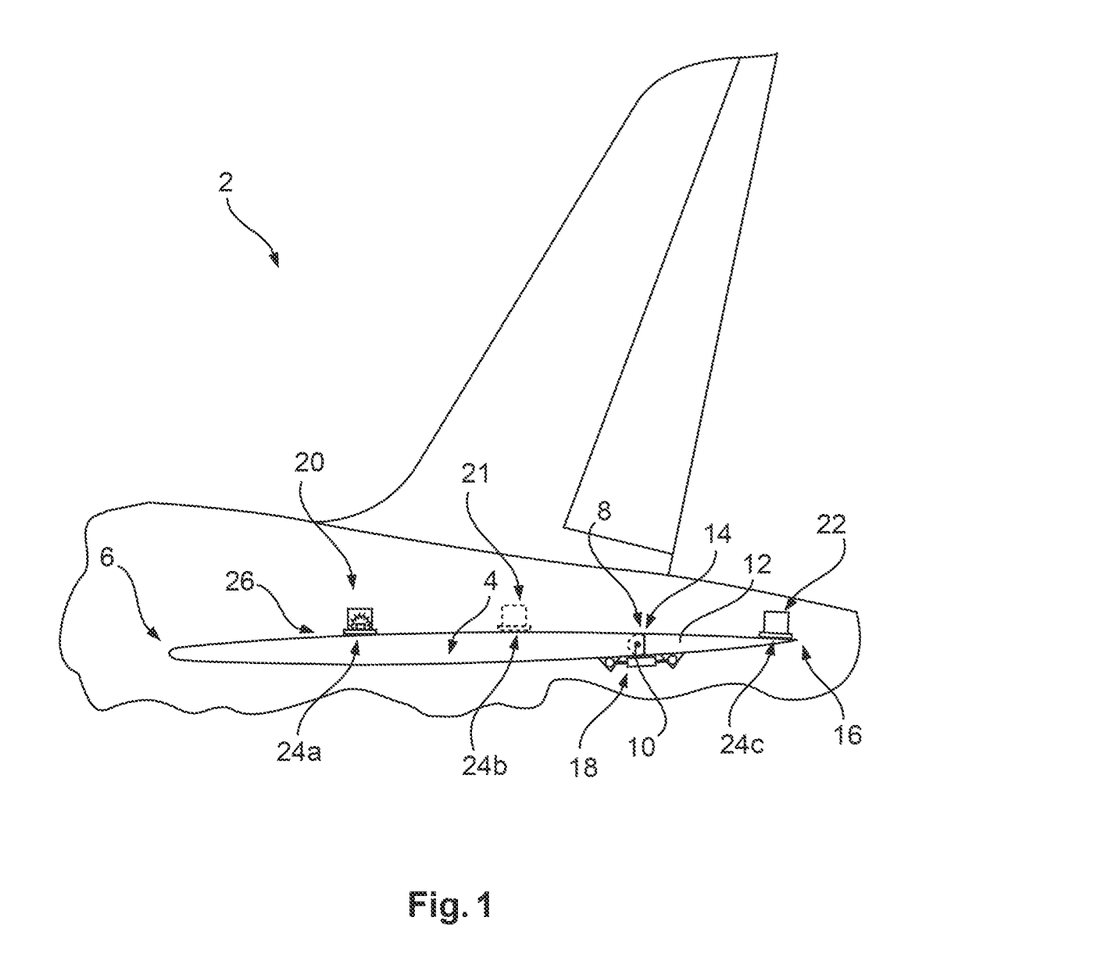
FIG. 1 shows a tail section of an aircraft with an elevator as an exemplary control surface to be rigged.

FIG. 1 shows a tail section of an aircraft 2 having a horizontal tail plane 4 with a leading edge 6 and a trailing edge 8 comprising a swivel axis 10 around which an elevator 12 is swivably mounted. The elevator 12 is designed as a flap having a leading edge 14 and a trailing edge 16. During the assembly of the aircraft 2 the elevator 12 is connected to an actuator 18 located between the elevator 12 and the horizontal tail plane 4. It is necessary to perform a fine-tuning of this connection, such that the actuator 18 is able to move the elevator 12 from one defined end position to a defined opposite end position. The end positions are predetermined under consideration of all occurring flight conditions and the elevator 12 must be adjustable to these end positions under all circumstances. Furthermore it must be assured that the elevator 12 can reliably be moved to a defined center position.

Due to the mechanical link of the actuator 18 to flanges (not shown in detail) on the horizontal tail plane 4 and the elevator 12 it is often necessary to re-adjust the length of an actuator rod or the position of connecting elements attached thereto. For this purpose after assembly of the horizontal tail plane 4, the elevator 12 and the actuator 18 input means in a cockpit of the aircraft 2 are commonly moved such that the elevator 12 is deflected. The mechanically resulting center position and the end positions are determined and compared to the predetermined center position and end positions. If there is a deviation between the predetermined positions and the measured positions a re-adjustment of the elevator 12 and the actuator 18 is necessary, as described above. This is repeated in an iterative process until the measured positions of the elevator 12 are within the predetermined limits. For redundancy reasons there may be more than just one actuator 18 connected to the elevator 12. Therefore, the rigging process is to be repeated for each of the actuators 18.

Measuring the positions of the elevator 12 may be conducted by using a first rigging component 20 and a second rigging component 22 according to the presentation in FIG. 1. Thereby, the first rigging component 20 may be placed onto a first reference point 24a on an upper surface 26 of the horizontal tail plane. Usually, such a first reference point 24a is used for placing a rigid reference bar explained further above. Using the same first reference point 24a for the first rigging component 20 avoids to change anything in the manufacturing process for the horizontal tail plane 4. As apparent from FIG. 1 the first reference point 24a is located relatively far away from the hinge line 10.

The second rigging component 22 is located in a region of the trailing edge 16 of the elevator 12 on a third reference point 24c. By deflecting the elevator 12 around the hinge line 10 the second rigging component 22 is moved upwards and downwards. The first rigging component 20 and the second rigging component 22 constitute an optical rigging apparatus. One of the two rigging components 20 and 22 is adapted for generating rays of light directed to the other rigging component. By deflecting the elevator 12 relative to the horizontal tail plane 4 a deviation in the relative spatial positions between the first rigging component 20 and the second rigging component 22 can easily be recognized through a visualization by means of the ray of light and/or by an electronic detection apparatus, such as an image sensor or a matrix of light sensitive diodes etc. The first rigging component 20 and the second rigging component 22 may be designed such that they clearly visualize a centered position when the elevator 12 is in an exactly centered position. This means that the first rigging component 20 and the second rigging component 22 comprise connecting surfaces that allow an exact alignment when placed on the respective reference points 24a and 24c.

A third measurement component 21 may further be placed between the first measurement component 20 and the second measurement component 22 onto a second reference point 24b. As explained further below, this third measurement component 21 may comprise an aperture.

Figure 2A:
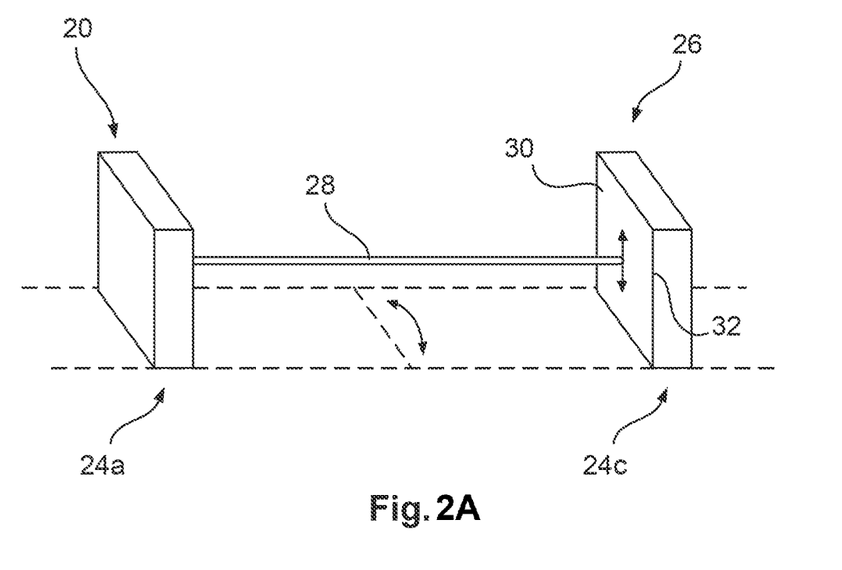
FIGS. 2A and 2B show the basic working principle of the optical rigging apparatus.
Figure 2B:
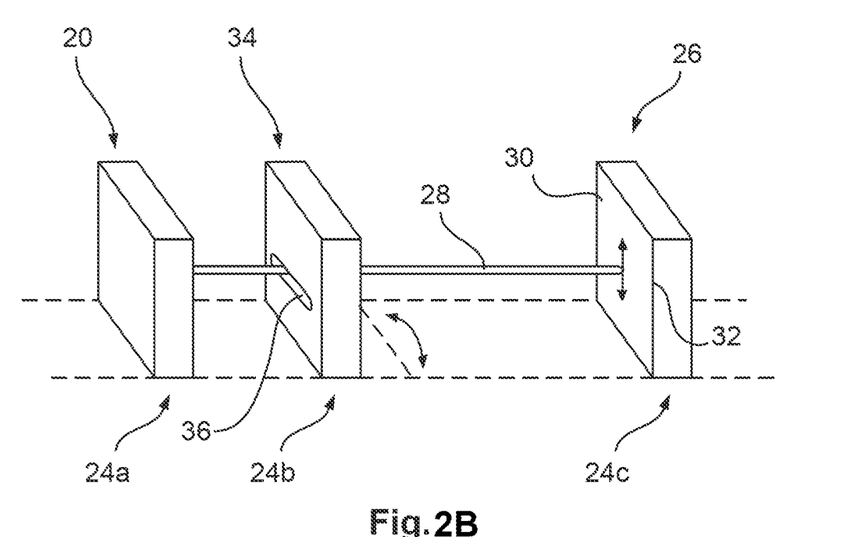

FIGS. 2A and 2B show basic working principles of the optical rigging apparatus having the first rigging component 20, the second rigging component 26 and an optional third measurement apparatus 24b. In the example of FIG. 2A the first rigging component 20 comprises a light emitting means that is adapted to emit rays of light 28 impinging on an indication surface 30 of the second rigging component 26. It is imaginable to provide an indication means, for example a scale, a grid array, at least one cross or a center point with another colour than the remaining parts of the indication surface 30. Additionally or alternatively, the indication surface 30 may comprise an electronic detector for identification of the position of the impinging rays of light.

By moving the elevator 12 up and down, an impinging light spot 32 moves down and up on the indication surface 30. By re-adjusting the connection of the actuator 18 to the elevator 12 the trajectory of the impinging spot 32 is altered. If the trajectory is satisfying for the operator or if the spot 32 in the neutral position of the elevator 12 is in a predetermined region of the indication surface 30, the rigging process is completed.

It has to be noted that the rigging process needs to be repeated for each actuator 18 connected to the elevator 12 as different hydraulic systems may be used for controlling the deflection of the elevator 12 due to the necessity of a redundant operation.

As shown in FIG. 2B, the first rigging component 20 and the second rigging component 26 may be completed by a third rigging component 34 with a horizontal slit or aperture 36 through which the light beam 28 can reach only in a predetermined elevator center position. This necessitates the exact placement of the third rigging component 34. As explained above, a reference bar is commonly positioned on two distanced reference points for being able to extend over the trailing edge of the elevator 12 without touching the upper surface of the horizontal tail plane 4 and the elevator 12 itself. The second reference point 24b may be used for placing the third rigging component 34 on the horizontal tail plane. A fine adjustment of it may be conducted by external laser-based measuring devices. If the light beam 28 cannot pass the aperture 36, there will not appear a light spot 32 on the indication surface 30.

Figure 3:
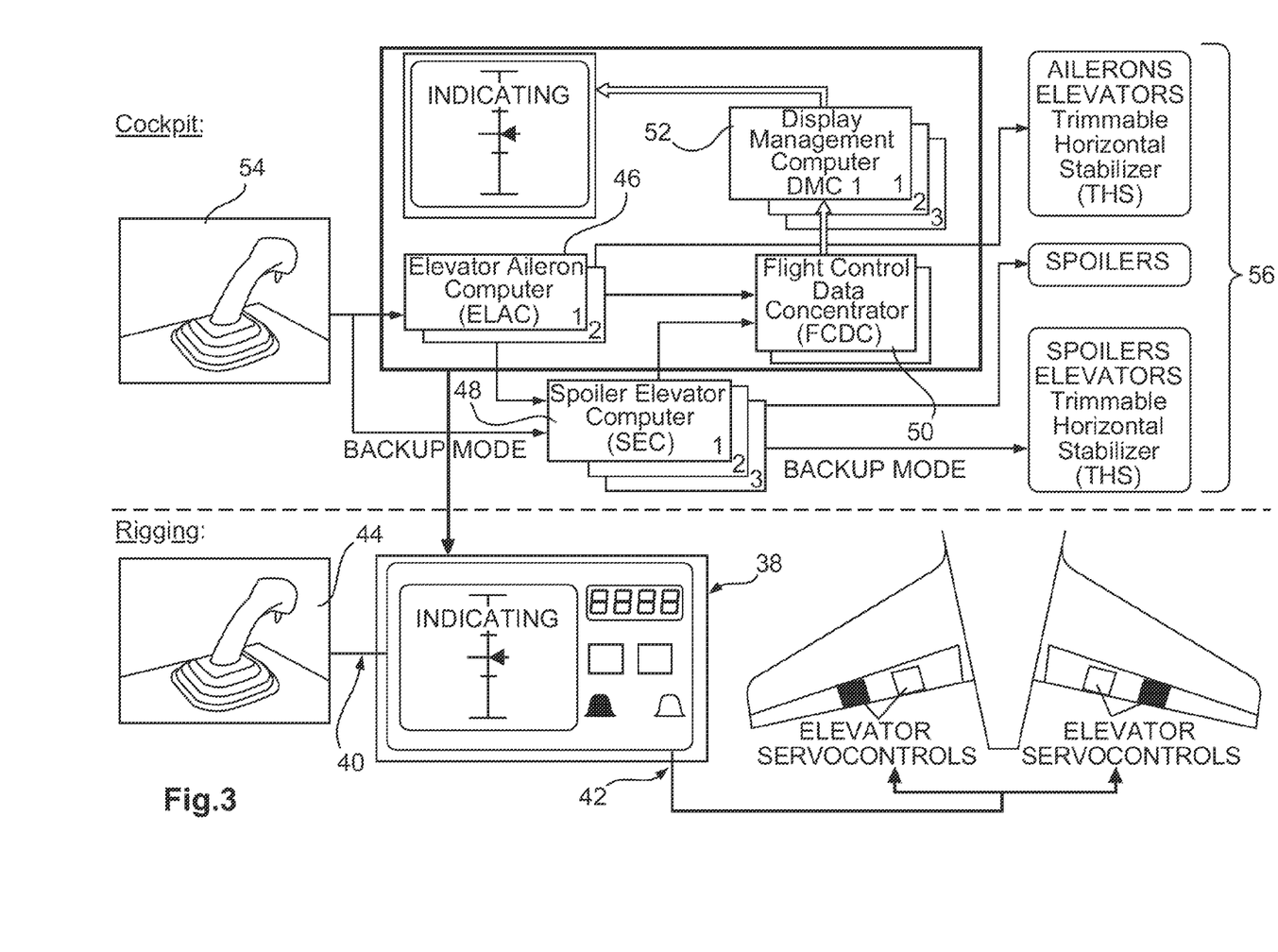
FIG. 3 shows the connection of a mobile control unit in the environment of an aircraft for the rigging process.

The whole rigging process may be conducted directly in the vicinity of the control surface, e.g. the elevator 12. Therefore, it is necessary to provide the required control signals for inducing the motion of the elevator 12. For this purpose, a mobile control unit 38 as shown in FIG. 3 is used.

The mobile control unit 38 comprises an input port 40 and an actuator interface 42, wherein the actuator interface 42 is exemplarily adapted for connecting actuators 18 or actuator control valves (not shown) to the mobile control unit 38. This may be realized by providing the mobile control unit with the ability to produce command signals for either controlling hydraulic valves or for providing position command signals. The input port 40 is designed for receiving input signals from an input means 44 such as a sidestick or any other similar input means, e.g. pilot controls. Generally, the mobile control unit 38 comprises an indication screen that allows to judge the commanded signals to ensure the generation of command signals for reaching a neutral or an end position of the control surface.

A core teaching of the present disclosure lies in the ability to temporarily replace the generation of command signals from a main flight control and flight management system of the respective aircraft with the generation of command signals from the mobile control unit 38 just for the purpose of moving the elevator 12 or any other control surface to be rigged.

For the purpose of clarification of a usual control landscape in a cockpit exemplarily an elevator aileron computer (ELAC) 46, a spoiler elevator computer (SEC) 48, a flight control data concentrator (FCDC) 50 and a display management computers (DMC) 52 connected to pilot controls 54 in the cockpit are presented. The pilot control 54 are commonly responsible for generating or inducing commands for moving spoilers, elevators, trimmable horizontal stabilizers and ailerons 56. The DMC are responsible for providing information on a screen.

During the rigging process this control landscape is substituted by the mobile control unit 38, which shows indications such as those generated by the display management computers 52, and routes command signals from input means 44 to the actuators 18 as if a pilot would induce these command signals by means of pilot controls 54. The mobile control unit 38 is thereby only a temporary replacement of any other control units as described above, and presents the same information as if an operator would conduct the same task in a cockpit of the aircraft 2.

As the mobile control unit 38 is portable, it may be brought directly into the vicinity of the elevator 12 such that an operator may move the input means 44 and measure the position of the control surface at the same time. This reduces the number of operators necessary for the whole rigging process.

By using the mobile control unit, the system and method for rigging according to the present disclosure a clear advantage regarding assembly and test time can be accomplished.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

What is claimed is:

1. A system for rigging a control surface of an aircraft that is movable relative to a reference structure of the aircraft by means of at least one actuator, the system comprising:
   a mobile control unit connectable to the at least one actuator,
   an input means providing a command signal for moving the control surface, and
   an optical rigging apparatus having a first rigging component and a second rigging component, the first rigging component fixed relative to the reference structure of the aircraft, and the second rigging component fixed relative to the control surface,
   wherein the optical rigging apparatus provides an indication of relative spatial positions of the first and second rigging components, and the mobile control unit generates an actuator signal for inducing a motion of the control surface based on the command signal of the input means.

2. The system of claim 1, wherein the mobile control unit generates a valve control signal controlling at least one actuator valve of the at least one actuator.

3. The system of claim 1, wherein the mobile control unit is further connectable to a control system of the aircraft.

4. The system of claim 1,
   wherein one of the first and second rigging components comprises a light source adapted for generating rays of light; and
   wherein the other one of the first and second rigging components comprises a light receiver in form of an indication surface, a detector or a reflector.

5. The system of claim 4, wherein the optical rigging apparatus comprises a third rigging component that includes an aperture, wherein the third rigging component is fixed relative to the reference structure of the aircraft between the first rigging component and the second rigging component in order to define a straight light beam between the light source and the light receiver.

6. The system of claim 1,
   wherein the mobile control unit comprises a display for indicating a position command of the input means.

7. The system of claim 1,
   wherein the second rigging component is fixed at a trailing edge of the control surface.

8. A method for rigging a control surface of an aircraft that is movable relative to a reference structure of the aircraft by means of at least one actuator, the method comprising:
   fixing a first rigging component relative to the reference structure;
   fixing a second rigging component relative to the control surface;
   connecting a mobile control unit to the at least one actuator;
   providing a command signal by using input means of the control unit;
   generating an actuator signal by means of the control unit for inducing a motion of the control surface based on the provided command signal;
   indicating a relative spatial position of the first and second rigging components by means of a light beam between the first and second rigging components; and
   adjusting the relative position between the control surface and the reference structure based on the indicated relative spatial position.

9. The method of claim 8, further comprising:
   re-indicating a relative spatial position of the first and second rigging components by means of a light beam between the first and second rigging components after adjusting; and
   re-adjusting the relative position between the control surface and the reference structure based on the re-indicated relative spatial position.

10. The method of claim 8, further comprising:
    indicating the command signal on a display of the control unit,
    wherein adjusting or re-adjusting is further based on the indicated command signal.

11. The method of claim 8, further comprising:
    fixing a third rigging component including an aperture relative to the reference structure of the aircraft between the first rigging component and the second rigging component in order to define the light beam between the light source and the light receiver.

12. The method of claim 8, wherein fixing the second rigging component relative to the control surface includes fixing the second rigging component at a trailing edge of the control surface.

13. A system for rigging a control surface of an aircraft that is movable relative to a reference structure of the aircraft by means of at least one actuator, the system comprising:
    a mobile control unit connectable to the at least one actuator,
    an input means providing a command signal for moving the control surface, and
    an optical rigging apparatus having a first rigging component, a second rigging component and a third rigging component, the first rigging component fixed relative to the reference structure of the aircraft, the second rigging component fixed relative to the control surface and the third rigging component fixed relative to the reference structure of the aircraft between the first rigging component and the second rigging component,
    wherein the optical rigging apparatus provides an indication of relative spatial positions of the first rigging component, second rigging component and third rigging component, and the mobile control unit generates an actuator signal for inducing a motion of the control surface based on the command signal of the input means.

14. The system of claim 13, wherein the mobile control unit generates a valve control signal controlling at least one actuator valve of the at least one actuator.

15. The system of claim 13, wherein the mobile control unit is further connectable to a control system of the aircraft.

16. The system of claim 13,
    wherein one of the first and second rigging components comprises a light source adapted for generating rays of light; and
    wherein the other one of the first and second rigging components comprises a light receiver in form of an indication surface, a detector or a reflector.

17. The system of claim 16, wherein the third rigging component includes an aperture, and the third rigging component is fixed relative to the reference structure of the aircraft between the first rigging component and the second rigging component in order to define a straight light beam between the light source and the light receiver.

18. The system of claim 13, wherein the mobile control unit comprises a display for indicating a position command of the input means.

19. The system of claim 13, wherein the second rigging component is fixed at a trailing edge of the control surface.

* * * * *